US00PP13193P2

(12) United States Plant Patent
Utecht

(10) Patent No.: US PP13,193 P2
(45) Date of Patent: Nov. 5, 2002

(54) GERANIUM PLANT NAMED 'FISROLISA'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,949

(22) Filed: Nov. 26, 2001

(65) Prior Publication Data

US 2002/0083501 P1 Jun. 27, 2002

(51) Int. Cl.[7] ..... A01H 5/00

(52) U.S. Cl. ..... Plt./328
(58) Field of Search ..... Plt./328

*Primary Examiner*—Kent L. Bell
(74) *Attorney, Agent, or Firm*—Foley & Lardner

(57) ABSTRACT

A new and distinct cultivar of geranium plant named 'Fisrolisa', as described and illustrated, and particularly characterized by the combined features of salmon-pink flower color with distinct almost white margin, relatively large, semi-spherical umbels, borne moderately low above the foliage, medium-green, relatively large leaves with distinct zonation, vigorous growth, wide, but relatively low plant habit, and moderately early flowering.

1 Drawing Sheet

BOTANICAL CLASSIFICATION

*Pelargonium zonale.*

VARIETY DENOMINATION

'Fisrolisa'.

BACKGROUND OF THE INVENTION

The present invention comprises a new and distinct cultivar of geranium, botanically known as *Pelargonim zonale*, and hereinafter referred to by the cultivar name 'Fisrolisa'.

'Fisrolisa' is a product of a planned breeding program which had the objective of creating new geranium varieties with deep salmon colored, semi-double flowers, and medium sized to moderately tall plant habit.

'Fisrolisa' originated from a hybridization made by the inventor, Angelika Utecht in a controlled breeding program in Galdar, Gran Canara, Spain, in 1995. The female parent was an unpatented hybrid seedling, no. K91-1216-3, having uniform salmon colored, single-type flowers, medium green foliage with strong zonation, and vigorous growth. The male parent of 'Fisrolisa' was the patented variety 'Fisglo', (U.S. Plant Pat. No. 7,394), characterized by orange-red, semi-double flowers, medium-green foliage with weak zonation, and medium sized, round plant habit.

'Fisrolisa' was selected as one flowering plant within the progeny of the stated cross by Angelika Utecht in 1996 in a controlled environment in Galdar, Gran Canaria, Spain. The first act of asexual reproduction of 'Fisrolisa' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1998, In Hillscheid, Federal Republic of Germany, and continuing thereafter, has demonstrated that the combination of characteristics as herein disclosed for 'Fisrolisa' are firmly fixed and are retained through successive generations of asexual reproduction. The new cultivar reproduces true to type.

'Fisrolisa' has not been observed under all possible environmental conditions. The phenotype may vary signficantly with variations in environment such as temperature, light intensity and day length. The following observations, measurements, and comparisons describe plants grown in Hillscheid, Germany, under greenhouse conditions which approximate those generally used in commercial practice.

BRIEF DESCRIPTION OF THE INVENTION

The following traits have been repeatedly observed and are determined to be basic characteristics of 'Fisrolisa' in combination distinguish this geranium as a new and distinct cultivar:

1. Bi-colored, salmon-pink and almost white, semi-double flowers;

2. Medium to large, round inflorescence, initially low, later at medium height above the foliage;

3. Medium green, relatively large, leaves with distinct zonation;

4. Vigorous growth, tall, but wide and moderately low plant habit; and

5. Early to medium spring flowering response.

Of the many commerical cultivars known to the present inventor, the most similar in comparison to 'Fisrolisa' is the patented variety 'Fistantut' (U.S. Plant Pat. No. 8,728). In comparison to 'Fistantut', 'Fisrolisa' has a slightly more salmon, less pink, flower color, shorter peduncles, larger leaves with stronger zonation, and more vigorous growth habit.

BRIEF DESCRIPTION OF THE DRAWING

The accompanying photographic drawing shows typical flower and foliage characteristics of 'Fisrolisa' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values and measurements were determined indoors from flowering plants grown developed in a green-house in May 2001, in Hillscheid, Germany, 10 weeks after planting of rooted cuttings. The plants were growing in 14 cm containers and had not been pinched.

Inflorescence:
- *Type.*—Umbel.
- *Shape.*—Semi-spherical.
- *Average diameter.*—98 mm.
- *Average depth.*—53 mm.
- *Peduncle length.*—108 mm.
- *Peduncle color.*—Light green, RHS 143 B, no anthocyanin.
- *Pedicel length.*—26 mm.
- *Pedicel color.*—Light green, RHS 144 A.
- *Number of flowers per umbel.*—About 20.

Corolla:
- *Average diameter.*—43 mm.
- *Form.*—Semi-double.
- *Shape.*—Round outline, occasionally flat, with a gap between upper and lower petals.
- *Number of petals.*—7–8.
- *Number of petaloids.*—0–2, narrow, same color as the petals.
- *Shape of petals.*—Narrow obovate, base attenuate, upper end is rounded, margin is entire.
- *Size of petals.*—Upper petals: Length 23–24 mm; width 20–21 mm. Lower petals: Length: 22–23 mm; width 22–23 mm.

Color (general tonality from a distance of three meters): Light salmon-pink and wide, almost white margin.
- *Color of upper petals.*—Main part RHS 43 D, margin RHS 56 A.
- *Markings of upper petals.*—None.
- *Color of lower petals.*—Main part RHS 43 D, margin RHS 56 A.
- *Markings of lower petals.*—None.
- *Color of lower surface of petals.*—Marbled, from RHS 49 B to 49 D.
- *Color of sepals.*—Outer surface light green, RHS 144 A to RHS 144 B; inner surface light green, RHS 144 A to RHS 144 B.
- *Number of sepals.*—5–6.
- *Shape of sepals.*—Linear to lanceolate, acute tip, truncate base, surface with moderate pubescence, margin entire.
- *Size of sepals.*—10–12 mm long, 4 mm wide for the largest upper sepal, 2–3 mm in width for the other sepals.

Bud (just before petals unfold):
- *Shape.*—Elliptical.
- *Color (sepals).*—Green, RHS 143 B to RHS 143 C.
- *Color (petals).*—RHS 155 A.
- *Length.*—18 mm.
- *Width.*—12 mm.

Reproductive organs:
- *Androecium.*—3–5 fertile anthers, filaments white, RHS 155 D, moderate pollen, orange, RHS 30 A.
- *Gynoecium.*—One pistil per flower, style and stigma salmon-pink, RHS 43 C, 5 to 6 lobed stigma.
- *Fertility/seed set.*—Occasionally a few seeds are developed. Fruit: Oblong, about 6 mm in diameter, with rostrum (beak), total length about 40 mm. Seed: Oblong, 4–5 mm long, brown, RHS 177 B.

Spring flowering response period: In Hillscheid, Germany in 2000, plants had on average 1.2 flowers opened 8 weeks after planting of rooted cuttings.

Outdoor flower production: Continuously flowering, the flower count in 2000, in Hillscheid, Germany, indicated about 2.3 inflorescences per plant in mid May.

Durability: Good stability of flower color, very little fading relatively good rain resistance.

Lastingness of the individual flower: About 8 days at 18° C., about 18 days for the umbel.

Fragrance: None.

Pest/disease resistance/susceptibility: No observations to date.

PLANT

Foliage:
- *Shape.*—Kidney-shaped to round, with closed to slightly open, cordate base, weak lobes.
- *Margin.*—Bicrenated, somewhat wavy.
- *Texture.*—Upper surface smooth, velvety.
- *Size of leaf.*—101 mm wide, 75 mm long.
- *Color of upper surface.*—Medium green, approximately RHS 137 C.
- *Color of zonation.*—Brown, about RHS 166 A.
- *Color of lower surface.*—RHS 137 D.
- *Petioles.*—50–60 mm long, 3 mm diameter, light green in color, approximately RHS 144 A.

General appearance and form:
- *Stem color.*—Green, RHS 144 B to RHS 144 D.
- *Internode length.*—10–15 mm.
- *Branching pattern.*—5.5 branches.
- *Size of plants.*—Height 13.9 cm, width 27.5 cm, as measured from the top of the soil (base of the main stem) to the surface of the foliage canopy, without inflorescences.

I claim:

1. A new and distinct cultivar of geranium plant named 'Fisrolisa', as described and illustrated herein.

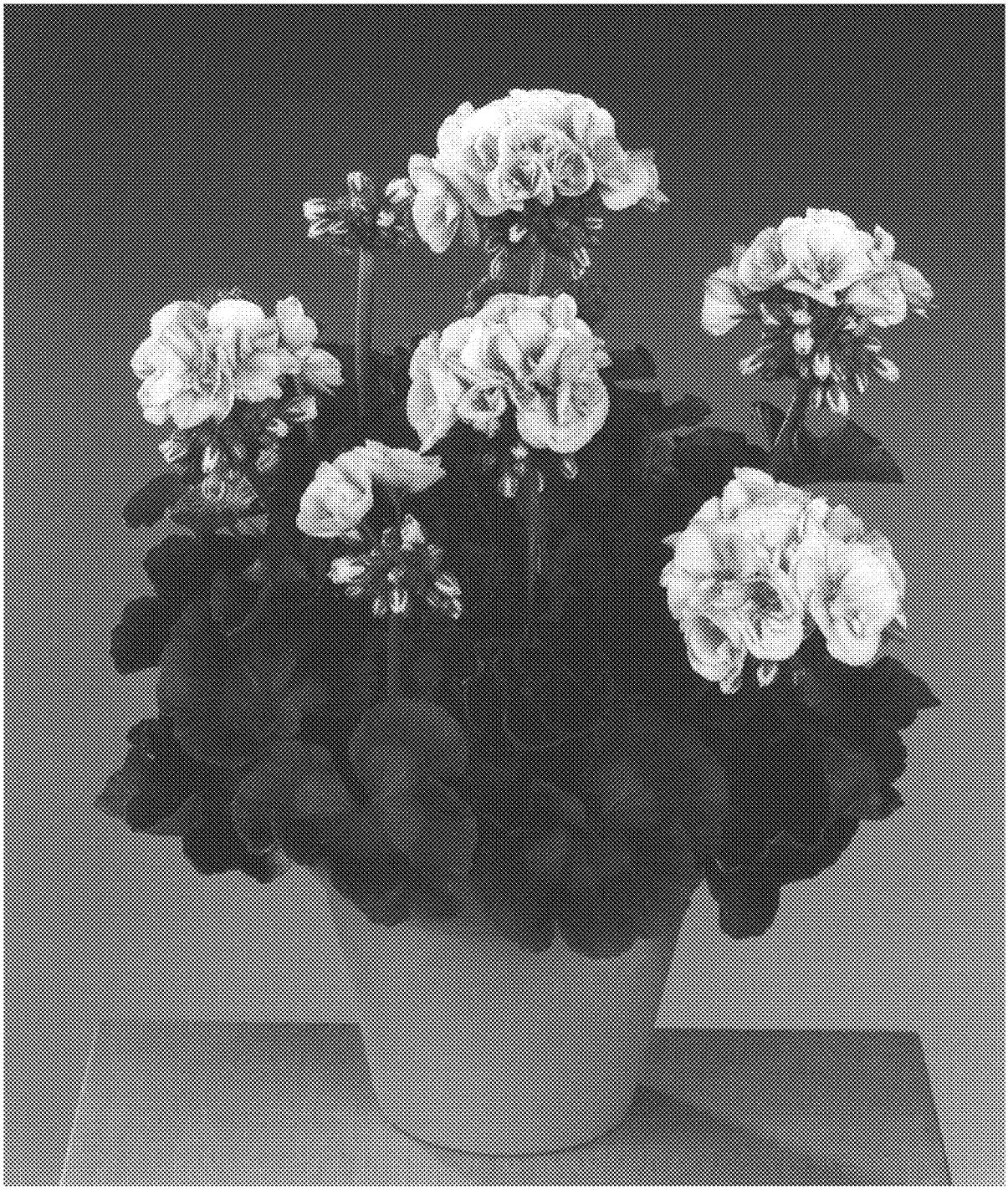

* * * * *